(12) United States Patent
Van Der Mark et al.

(10) Patent No.: US 9,599,550 B2
(45) Date of Patent: Mar. 21, 2017

(54) ANALYSIS AND CONTROL OF AEROSOL FLOW

(71) Applicant: KONINKLIJKE PHILIPS N.V., Eindhoven (NL)

(72) Inventors: Martinus Bernardus Van Der Mark, Best (NL); Alphonsus Tarcisius Jozef Maria Schipper, Stamproy (NL); Jeroen Herman Lammers, Eindhoven (NL); Alwin Rogier Martijn Verschueren, 'S-Hertogenbosch (NL); Henri Marie Joseph Boots, Best (NL); Petrus Henricus Cornelius Bentvelsen, Waalre (NL); Hendrik Huijgen, Eindhoven (NL); Paul Van Der Sluis, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 235 days.

(21) Appl. No.: 14/354,626

(22) PCT Filed: Oct. 23, 2012

(86) PCT No.: PCT/IB2012/055825
§ 371 (c)(1),
(2) Date: Apr. 28, 2014

(87) PCT Pub. No.: WO2013/061248
PCT Pub. Date: May 2, 2013

(65) Prior Publication Data
US 2015/0020804 A1 Jan. 22, 2015

Related U.S. Application Data

(60) Provisional application No. 61/552,507, filed on Oct. 28, 2011.

(51) Int. Cl.
*G01N 15/02* (2006.01)
*A61M 11/00* (2006.01)
(Continued)

(52) U.S. Cl.
CPC ......... *G01N 15/0205* (2013.01); *A61M 11/00* (2013.01); *A61M 16/0003* (2014.02);
(Continued)

(58) Field of Classification Search
CPC ...... G01N 15/02; G01N 15/0205; G01N 9/00; G01N 21/532; A61M 16/0051; B05B 12/082
(Continued)

(56) References Cited

U.S. PATENT DOCUMENTS 4,211,487 A 7/1980 Morrison
4,518,861 A 5/1985 Krempl et al.
(Continued)

FOREIGN PATENT DOCUMENTS

EP 877345 11/1998
JP 2002116142 A 4/2002
(Continued)

OTHER PUBLICATIONS

C.S. Tsai et al., "Miniaturized Multiple Fourier-Horn Ultrasonic Droplet Generators for Biomedical Applications", Lab Chip, 2010, 10, pp. 2733-2740.
(Continued)

*Primary Examiner* — Roy M Punnoose
(74) *Attorney, Agent, or Firm* — Michael W. Haas

(57) ABSTRACT

An aerosol generation system has a light source arrangement which provides signals at first and second wavelengths, and the detected light signals are recorded. The detected signals are processed to derive at least a measure of the aerosol particle size. This can be used in combination with the other
(Continued)

parameters which are conventionally measured, namely the aerosol density and flow velocity. Thus, optical measurement (possibly in combination with an air flow measurement) can be used to estimate the aerosol output rate as well as the particle size.

15 Claims, 4 Drawing Sheets

(51) Int. Cl.
  *B05B 12/08* (2006.01)
  *G01N 21/53* (2006.01)
  *A61M 16/00* (2006.01)
  *A61M 16/14* (2006.01)
  *G01N 9/00* (2006.01)
  *G01N 21/64* (2006.01)
  *B05B 17/00* (2006.01)

(52) U.S. Cl.
  CPC ........ *A61M 16/0051* (2013.01); *A61M 16/14* (2013.01); *B05B 12/082* (2013.01); *G01N 9/00* (2013.01); *G01N 15/0211* (2013.01); *G01N 21/53* (2013.01); *G01N 21/6445* (2013.01); *A61M 11/001* (2014.02); *A61M 11/005* (2013.01); *A61M 2205/3306* (2013.01); *A61M 2205/3327* (2013.01); *A61M 2209/02* (2013.01); *B05B 17/0646* (2013.01); *G01N 21/532* (2013.01); *G01N 21/534* (2013.01); *G01N 2021/6439* (2013.01)

(58) Field of Classification Search
  USPC ........................................................ 356/335
  See application file for complete search history.

(56) References Cited

U.S. PATENT DOCUMENTS

| | | | |
|---|---|---|---|
| 5,826,570 | A | 10/1998 | Goodman et al. |
| 7,126,687 | B2* | 10/2006 | Hill ........................ G01N 21/64 356/336 |
| 2001/0010223 | A1 | 8/2001 | Gonda |
| 2001/0173743 | | 9/2004 | Valaskovic et al. |
| 2004/0173743 | A1 | 9/2004 | Valaskovic |
| 2006/0102178 | A1 | 5/2006 | Feiner et al. |
| 2007/0299561 | A1 | 12/2007 | Montaser et al. |
| 2008/0204746 | A1* | 8/2008 | Gonzalez Cruz ..... G01J 3/4406 356/319 |
| 2008/0285032 | A1 | 11/2008 | Ohkubo |
| 2011/0079220 | A1 | 4/2011 | Altobelli et al. |
| 2013/0135607 | A1* | 5/2013 | Wedler ................... G01N 21/53 356/51 |

FOREIGN PATENT DOCUMENTS

| | | |
|---|---|---|
| JP | 2002165882 A | 6/2002 |
| JP | 2008039539 A | 2/2008 |
| WO | WO0236190 | 5/2002 |
| WO | WO02065088 | 8/2002 |
| WO | WO2013042002 A1 | 3/2013 |

OTHER PUBLICATIONS

Schipper A. et al., "I-Neb II Design Descriptions", APT513-08-5484 C07 Philips Applied Technologies, Mar. 2009, pp. 1-15.
Van Der Mark M.B.et al, "Propagation of Light in Disordered Media" PhD thesis (1990).
Van De Hulst et al., "Light Scattering by Small Particles", Physics Today, 10(12), 28 (1957); (Dover, New York, 1981).
Bentvelsen Peter et al., "Development Report I-neb II Nephelometer" Respironics Respiratory Drug Delivery (UK) Ltd, Report No. APX-11-0271, (Apr. 1, 2011).

* cited by examiner

FIG. 1

FIG. 2 aerosol distribution and optical density

FIG. 7 aerosol optical density per wavelength

FIG. 8

ANALYSIS AND CONTROL OF AEROSOL FLOW

CROSS-REFERENCE TO PRIOR APPLICATIONS

This application is the U.S. National Phase application under 35 U.S.C. §371 of International Application Serial No. PCT/IB2012/055825, filed on Oct. 23, 2012, which claims the benefit of U.S. Application Ser. No. 61/552,507, filed on Oct. 28, 2011. These applications are hereby incorporated by reference herein.

TECHNICAL FIELD OF THE INVENTION

This invention relates to the analysis of an aerosol flow.

BACKGROUND TO THE INVENTION

A nebulizer is a drug delivery system by aerosol into the lungs, and is used to treat diseases such as Cystic Fibroses, COPD and Asthma. A number of companies make devices for respiratory drug delivery by aerosol. Preferably the devices are compact, portable, battery operated and light-weight.

Nebulizers generate an aerosol flow, and the patient receives a specific amount of medication in the form of small droplets (aerosol) that are typically formed by forcing the medication through a mesh in the form of a thin metal plate with tiny holes.

The volume of medication to be nebulized (typically 0.2 to 2 ml) is dosed into the device, and the device generates the aerosol by means of well known methods such as a vibrating mesh as mentioned above, or a vibrating horn, or vibrating flat plate in a resonant cavity. The required ultrasonic vibration is generated by an actuator, typically a piezoelectric crystal. The amount of medication that reaches the patient during the treatment is equal to the supplied medication dose minus the aerosol deposited in the device and residues of medication that remain in the device after the treatment is finished.

The proper medical dosage of a nebulizer is essentially dependent on the output volume, but correct application of the dose can also depend on the particle size of the aerosol in which the drug is dissolved. The output volume varies with aging of the output mesh of the nebulizer because the mesh will deteriorate over time, for example due to clogging of the thousands of tiny holes (~2.5 micron diameter conical holes). The viscosity of the medicine may also change with temperature, and hence change the output.

The breathing pattern of the patient is also of importance. In current systems, aerosol density and particle size are not measured, let alone used to give feedback to the system or patient. This may lead to under dosage, over dosage, waste of drug, unnecessary contamination of the environment and higher costs.

For a medication therapy, it is sometimes required that not only the dose is precisely defined, but also the rate at which the medication is delivered, namely the aerosol output rate. The nebulizer generally controls the aerosol output rate by means of the electrical power and driving frequency applied to the piezoelectric drive system.

The aerosol output rate cannot be exactly predicted based on the applied electrical power. Aerosol generating systems may have different efficiencies (amount of aerosol generated per unit electrical power), for example due to device and mesh tolerances, temperature, and cleanliness of the mesh.

A system has been proposed that estimates the aerosol output rate by measuring the density of the aerosol beam, which is then used in a feedback control loop to adjust the electrical power. The aerosol density can be measured by means of an optical beam perpendicular to the aerosol beam. The optical beam can be generated by a light emitting diode (LED). The beam shape of the light from a LED is divergent, and the optical beam may be collimated to a parallel or nearly parallel beam using one or more lenses or mirrors. The beam may be further shaped using a circular or rectangular diaphragm.

The optical beam crosses the aerosol beam, and falls on an optical sensor (optionally through a diaphragm and optionally focused using one or more lenses). The optical system can be calibrated by measuring the sensor signal at a time that no aerosol is present with the LED off ("dark signal") and with the LED on ("light signal"). If the aerosol beam is present, the rays of the optical beam are scattered by the droplets, thus decreasing the light that falls on the optical sensor, and hence decreasing the measured output signal at the optical sensor. The decrease of light on the sensor caused by droplets in the light path is called obscuration. The obscuration can be quantitatively expressed by the parameter ("light signal"–"measured signal")/("light signal"–"dark signal").

The obscuration is a function of the droplet density in the aerosol beam and the length over which the light travels through the aerosol beam. If the velocity of the aerosol beam is known, e.g. through a separate air flow rate measurement (using a differential pressure sensor or a flow sensor), then the aerosol output rate can be computed from the aerosol density and the volume of the aerosol beam that passes the optical beam per unit of time. The volume can be calculated from the product of the cross-sectional area of the aerosol beam and the velocity of the aerosol beam.

The level of obscuration by itself does not give any indication of aerosol density nor particle size. Only if the particle size is known can the aerosol density be derived from the obscuration. In practice, the nominal particle size is often mostly predetermined by the design and construction of the complete aerosol generator.

However, it is desirable to know the particle size, either to give an indication of the performance of the aerosol generating system (for example to provide an indication of ageing) or because certain particle sizes are desired for particular absorption characteristics, so that particle size becomes a parameter which characterizes the performance of the system.

SUMMARY OF THE INVENTION

According to the invention, there is provided an aerosol generation system, comprising:
a flow device for generating an aerosol flow;
a light source arrangement and a light detector for detecting light which has interacted with the aerosol flow;
a controller for controlling the light source arrangement and for interpreting the detected light signals;
wherein the controller is adapted to:
control the light source arrangement to provide a first signal at a first wavelength and to record a first detected light signal;
control the light source arrangement to provide a second signal at a second wavelength and to record a second detected light signal;
process the first and second detected signals to derive a measure of the aerosol particle size.

The invention is based on the recognition that light sensing can be used to derive a particle size parameter of the aerosol flow, as well as the conventional derivation of particle density (otherwise known as the volume fraction). In particular, by providing measurement with at least two wavelengths, the extra degree of freedom enables the particle density as well as the particle size to be determined.

The light detector can be for detecting light which has passed through the aerosol flow, thus measuring obscuration. In this case, a dye can be added to the aerosol liquid to increase the absorption and thereby increase the signal strength.

Alternatively, the light detector can be for detecting light which has been reflected or scattered by the aerosol flow. In this case, a fluorescent additive can be added to the aerosol liquid, which is excited by the light source light, again to increase the signal strength. The absorption and scattering approaches can be used in combination.

The controller can be further adapted to derive the aerosol density from the detected light signals. Thus, the system can provide density and particle size information.

The light source arrangement can comprise light sources at different positions along the aerosol flow, and a detector is then provided for each light source, wherein the controller is adapted to derive the aerosol velocity from the detected light signals at the different positions along the aerosol flow. A cross correlation can be applied to the signals received at the different positions along the aerosol flow with a variable time delay, thereby to determine a time delay of the aerosol flow between the different positions. This then enables the velocity to be measured.

The light detector can be adapted to separate polarized and depolarized light contributions to determine an amount of scattering.

A flow device controller can be used for controlling the flow device, and the system can comprise a feedback loop such that the flow device controller takes account of monitored parameters (particle size and optionally one or more of particle density and flow velocity) of the aerosol flow. The flow device control can be based on the electric power and/or duty cycle.

The invention also provides a method of generating an aerosol, comprising:
generating an aerosol flow;
controlling a light source arrangement to provide a first signal at a first wavelength and recording a first detected light signal;
controlling the light source arrangement to provide a second signal at a second wavelength and recording a second detected light signal;
processing the first and second detected signals to derive a measure of the aerosol particle size.

BRIEF DESCRIPTION OF THE DRAWINGS

Examples of the invention will now be described in detail with reference to the accompanying drawings, in which:

FIG. 1 shows an example of aerosol generation system of the invention;

FIG. 2 shows how the aerosol flow interacts with the light detection system;

FIG. 7 shows how different wavelengths of light give obscuration profiles with respect to particle size that are different; and FIG. 8 shows how different particle sizes give different relative volume and obscuration.

DETAILED DESCRIPTION OF THE PREFERRED EMBODIMENTS

Figure 3:
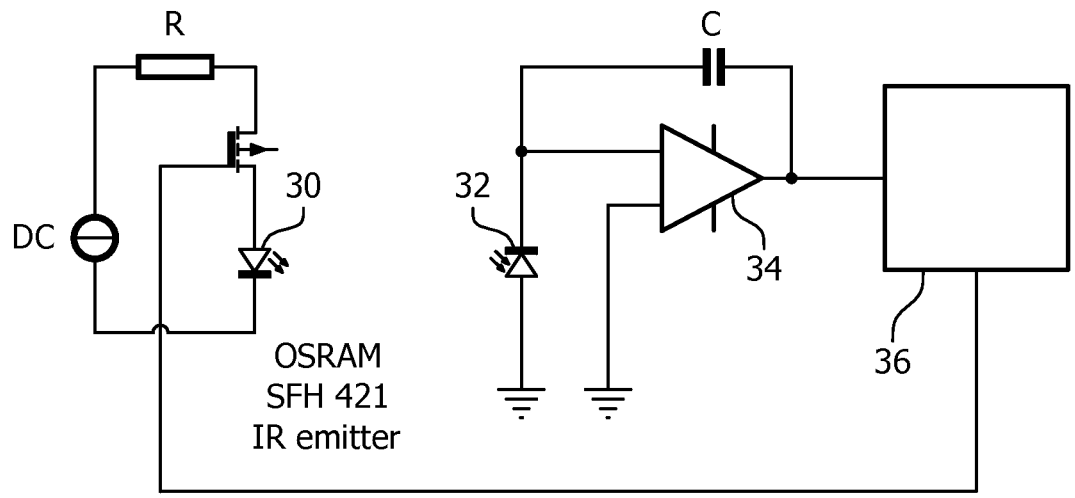
FIG. 3 shows the an electrical circuit for controlling a light source and associated detector.

The invention provides an aerosol generation system in which a light source arrangement provides signals at first and second wavelengths, and the detected light signals are recorded. The detected signals are processed to derive at least a measure of the aerosol particle size. This can be used in combination with the other parameters which are conventionally measured, namely the aerosol density and flow velocity. Thus, optical measurement (possibly in combination with an air flow measurement) can be used to estimate the aerosol output rate as well as the particle size.

Figures 1, 2:
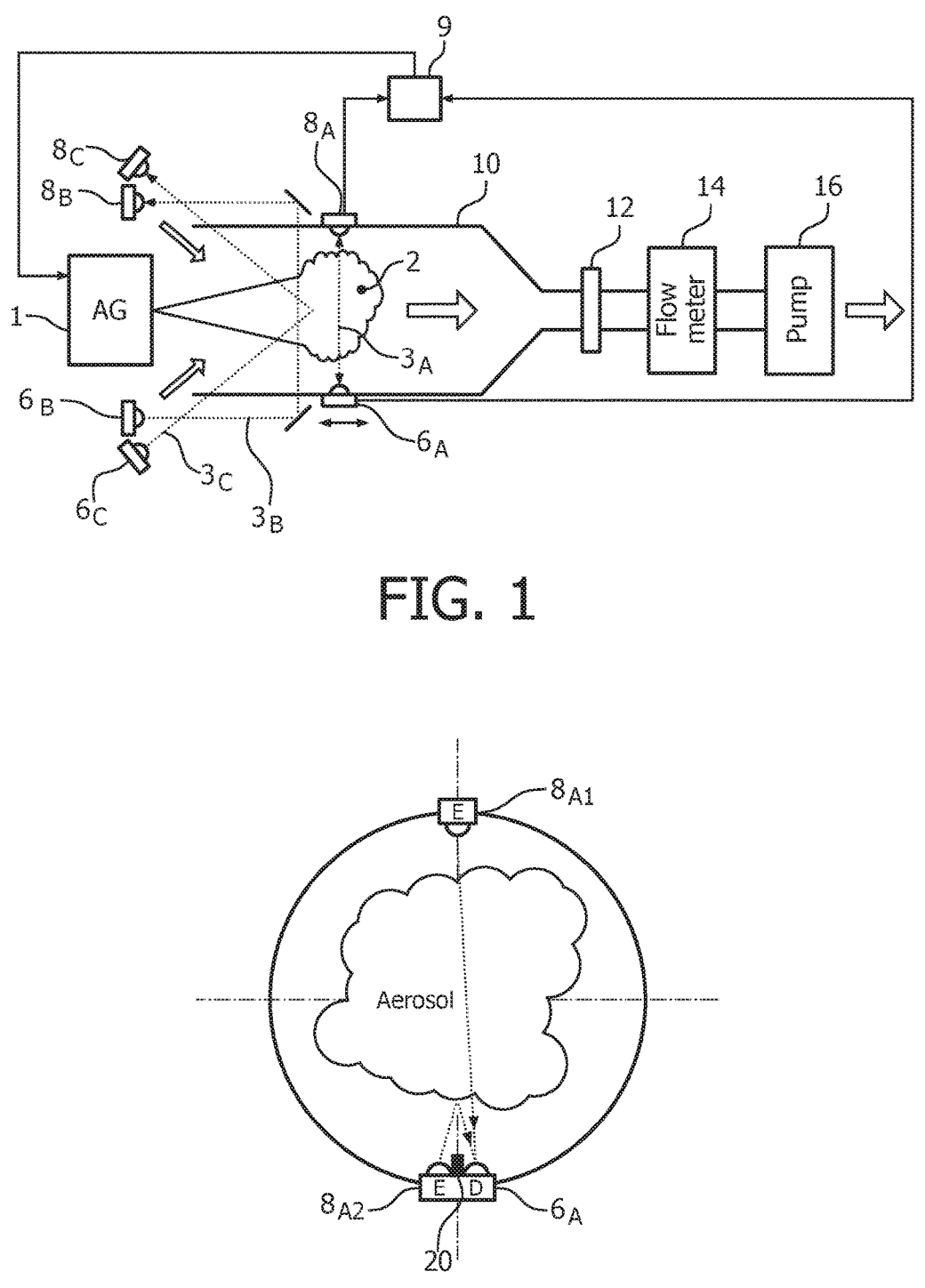

FIGS. 1 and 2 show an example of system of the invention. In FIG. 1, the system of the invention is combined with a system able to carry out a performance test. The system may be external to or internal to a nebulizer.

The system comprises an aerosol generator 1, which is for example a piezoelectric driven aerosol generation system 1, and a controller 9. The aerosol 2 is generated using a mesh. An optical system generates a beam (see, e.g., beam paths $3_A$, $3_B$, and $3_C$) at distance from the mesh.

FIG. 1 shows three possible beam paths, as $3_A$, $3_B$, and $3_C$.

The optical system consists of a light source 6 (for the three possible beam configurations, the light source is shown as $6_A$, $6_B$ and $6_C$) with optional lens and diaphragm, and an optical detector 8 (for the three possible beam configurations, the light detector source is shown as $8_A$, $8_B$ and $8_C$) with optional lens and diaphragm. In the illustrated embodiment, communication takes place between controller (9), light source(s) (6, $6_A$, $6_B$ and $6_C$), light detector (8, $8_A$, $8_B$ and $8_C$), and aerosol generation system 1 in a feedback loop fashion as shown.

The first beam path $3_A$ between the light source $6_A$ and detector $8_A$ is perpendicularly across the aerosol flow. The second beam path $3_B$ between the light source $6_B$ and detector $8_B$ involves the introduction of the light signal in the direction of flow, using a first reflector to redirect the light into a transverse direction, and using a second reflector to redirect the light again parallel to the flow direction to the sensor.

The third beam path $3_C$ between the light source $6_C$ and detector $8_C$ involves the introduction of the light signal diagonally into the aerosol flow, with reflection or scattering detected by the sensor.

The different flow paths are provided within a flow tube 10.

FIG. 1 also shows performance test equipment in the form of a filter 12, flow meter 14 and pump 16. These are not part of the nebulizer, but part of the experimental set up. Typically, in normal use the pump 16 is replaced by the lungs of the patient.

The system may use one or more of the beam paths shown in FIG. 1.

The aerosol generation system 1 is driven by a signal from a drive circuit. The drive signal may be a high frequency signal that is modulated at a lower frequency. The output power may be controlled by either the amplitude of the signal, the duty cycle of the modulation, or both.

The output power of the drive circuit is set by an input signal from a power control feedback system (not shown).

If the light path is internal to the nebulizer, this allows for a blank intensity calibration when the aerosol generator is switched off.

The system of FIG. 1 is for implementing optical aerosol density measurements (nephelometer) and additionally to provide particle size information.

FIG. 2 shows the optical set up for path A as a cross section through the mouth piece section, directly across the aerosol. In addition, FIG. 2 shows an arrangement in which transmission as well as reflection is monitored.

For this purpose, there is one detector $6_A$. One emitter $8_{A1}$ is placed opposite to the detector for transmission measurements. Another emitter $8_{A2}$ is placed next to the detector, but with a light shield 20 between. This is used for reflection measurements. The light shield reduces direct coupling of light into the detector.

FIG. 3 shows the electrical circuit diagram, for one light source and detector pair.

The LED IR emitter 30 for example has a peak wavelength of 880 nm. A typical example of the radiant flux is 23 mW at 100 mA forward current. The radiant intensity in the axial direction typically 7 mW/sr. Only one emitter circuit is shown in FIG. 3 (the emitter, a drive transistor 30, a dc voltage source and a load resistor), but there will be two such circuits to implement the two emitters shown in FIG. 2. Furthermore, there are multiple emitter and detector circuit combinations to provide operation at different frequencies, as explained further below.

The detector 32 is a photo diode, tuned to have the peak sensitivity at the emitter wavelength (880 nm). A typical sensitivity is 0.65 A/W, and an active area 2.65×2.65 mm The detector output in the form of a photocurrent is integrated by an integrator 34. An A/D converter 36 detects the slope of the voltage on the integrator, which is proportional to the amount of light. This can for example comprise a 16 bit Sigma Delta A/D converter embedded in a microcontroller.

Calibration measurements are carried out before system operation. These will depend on the optical path being used. For the arrangement of FIG. 2, a dark measurement of the photo diode is recorded, with the emitters off. A transmission reference measurement involves measuring the transmission without aerosol present, but with the transmission emitter $8_{A1}$ on. A reflection reference measurement involves measuring the reflection without aerosol present, but with the reflection emitter $8_{A2}$ on. These three measurements are all used for calibration purposes.

The signal measurement comprises a transmission measurement in which the transmission through the aerosol is measured and a reflection measurement in which the reflection by the aerosol is measured.

A measurement procedure comprises:

Perform dark measurement;

Perform transmission reference measurement, subtract dark measurement to derive a first transmission value Tr;

Perform reflection reference measurement, subtract dark measurement to obtain a first reflection value Rr;

Switch on aerosol generator;

Perform dark measurement;

Perform transmission measurement, subtract dark measurement to derive a second transmission value T;

Perform reflection measurement, subtract dark measurement to derive a second reflection value R.

The transmission level is then interpreted as Transmission=T−Tr and the reflection level is interpreted as Reflection=R−Rr. These values can then be used to derive aerosol density information (in known manner) and can be combined with flow velocity to derive output rate (again in known manner).

Figure 4:
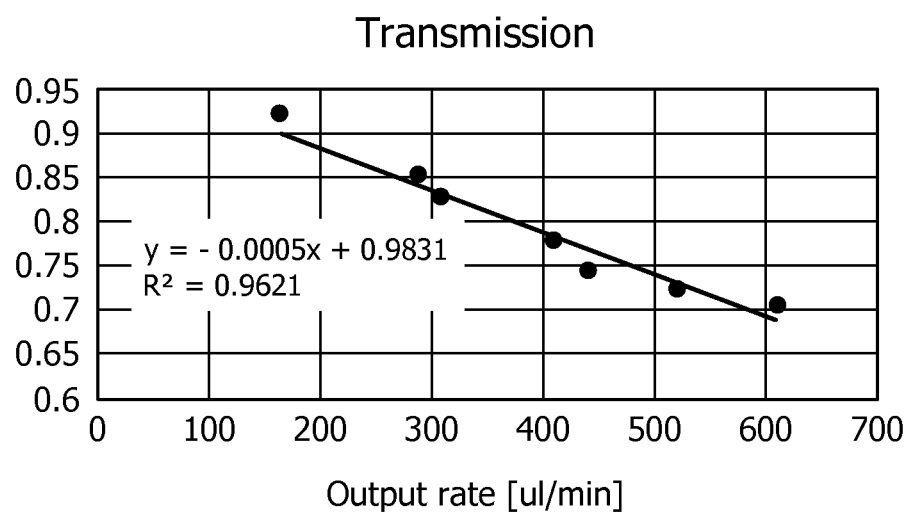
FIG. 4 is used to explain how transmission through the aerosol is dependent on the flow rate.

FIG. 4 shows the optical transmission percentage (with respect to a clear path) versus aerosol output rate.

The aerosol output rate and aerosol density scale linearly with each other. All aerosol comes through the same channel at any time, so the setting of pump speed (as part of the testing process) determines the dilution of the aerosol with air and hence determines the ratio between aerosol density and aerosol output.

Figure 5:
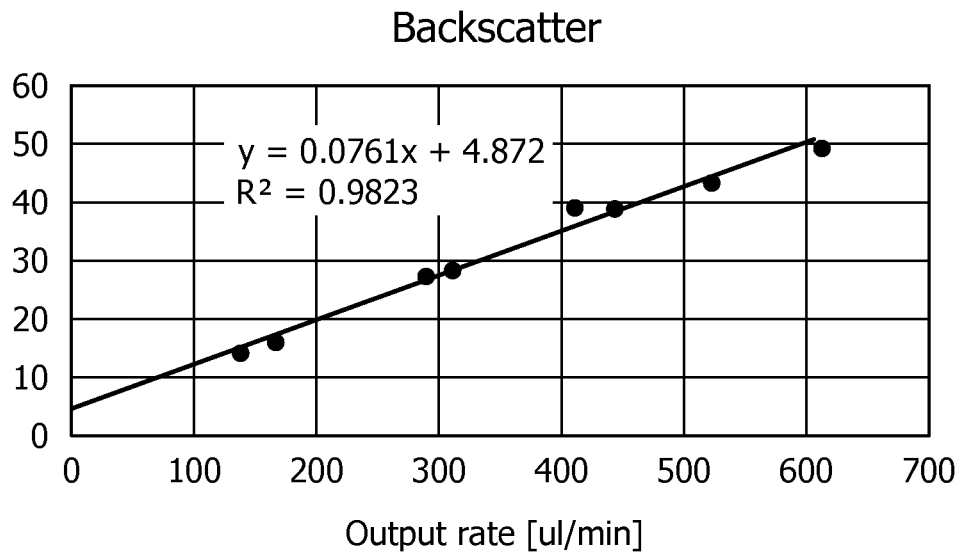
FIG. 5 is used to explain how scattering from the aerosol is dependent on the flow rate.

FIG. 5 shows the backscattering efficiency as a function of aerosol output rate in arbitrary units.

FIGS. 4 and 5 show the result of the test set up, and show that the invention can work.

The optical detector information does not give any indication of the particle size. To explain how the invention enables particle size to be determined, analysis based on scattering theory is required.

Diffusively scattering media, such as milk, mist or (white) paint, also called "diffusers", "random media" or "turbid media", are characterized by at least four parameters (reference is made to "Miniaturized multiple Fourier-horn ultrasonic droplet generators for biomedical applications" by Chen Tsai et al, Lab Chip 2010, 10, pp 2733-2740 and H. C. van de Hulst, "Light scattering by small particles", (Dover, N.Y., 1981)):

The so-called extinction length $l_{ext}$, which is the characteristic for loss of intensity in the directly transmitted (unscattered) light: $I=I_0 \exp(-z/l_{ext})$ due to both absorption and scattering, where $I_0$ is the incident intensity. For substantially white (non-absorbing) media $l_{ext}$ should be replaced with $l_{sca}$, the scattering mean-free path;

The so-called transport mean-free path $l_{tra}$ (sometimes also referred to as the reduced scattering length), which is the effective diffusion length in the bulk of the scattering medium. It is the characteristic length over which the light loses correlation with its original propagation direction;

The absorption length $l_{abs}$, which is indicative of the "whiteness" of the medium;

The size or thickness d of the medium.

The difference between the scattering mean free path $l_{sca}$ and transport mean free path $l_{tra}$ is a consequence of anisotropic scattering. The following relation holds:

$$l_{tra}=l_{sca}/(1-\langle \cos\theta \rangle)$$

where θ is the scattering angle. If the particles scatter equal amounts of light in all directions then the mean cosine of the scattering angle is zero and hence $l_{tra}=l_{sca}$.

Figure 6:
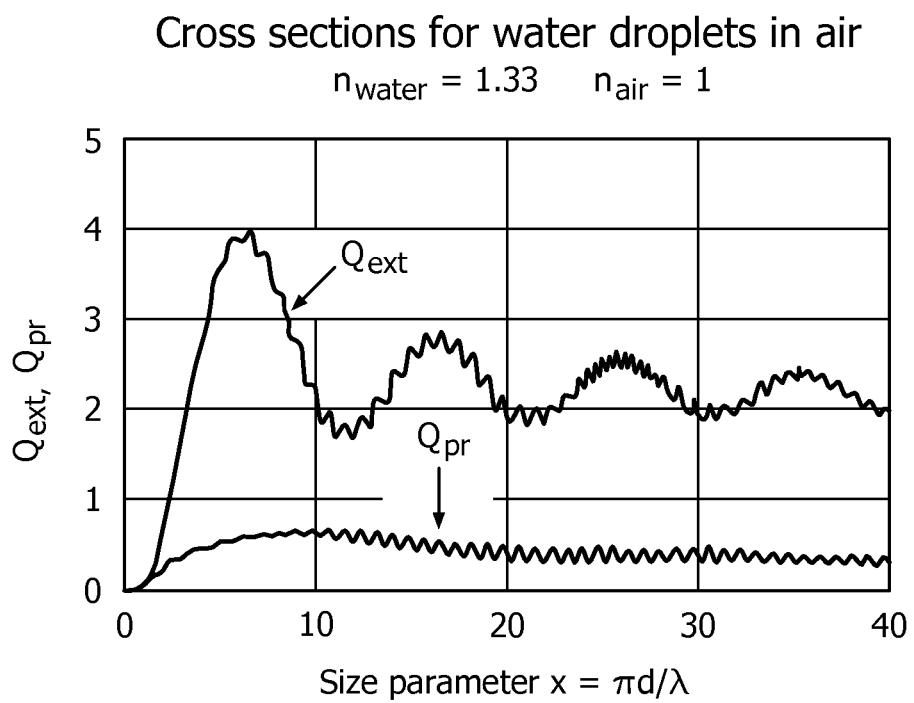
FIG. 6 shows how various parameters vary with particle size.

In the above, the (statistical) homogeneity of the medium in both space and time is assumed. All parameters mentioned relate in some way or another to the optical density of the medium. In a statistically homogeneous medium of volume V, the following relations hold (in which r is the particle radius, n the particle refractive index, $n_{med}$ the refractive index of the medium, λ the wavelength in vacuum, N the number of particles and $n_0=N/V$ the number density of particles):

volume fraction: $f=4\pi r3n_0/3$, $0<f<1$, typically for packed spheres $f<0.74$ size parameter: $x=2\pi r\, n_{med}/\lambda$ geometric cross section: $\sigma_{geo}=\pi r^2$ scattering cross section: $\sigma_{sca}$ absorption cross section: $\sigma_{abs}$ total cross section or extinction cross section: $\sigma_{ext}=\sigma_{sca}+\sigma_{abs}$ extinction length: $l_{ext}=(n_0\sigma_{ext})^{-1}$
particle "whiteness" or albedo: $a=\sigma_{sca}/\sigma_{ext}$
quality factor for scattering: $Q_{sca}=\sigma_{sca}/\sigma_{geo}$
scattering mean free path: $l_{sca}=(n_0\sigma_{sca})^{-1}$
scattering coefficient: $\mu_s=1/lsca$
inelastic length: $l_{in}=al_{sca}/(1-a)=l_{ext}/(1-l_{ext}/l_{sca})=(l_{ext}^{-1}-lsca^{-1})^{-1}$
cross section for radiation pressure: $\sigma_{pr}$
quality factor for momentum transfer: $Q_{pr}=\sigma_{pr}/\sigma_{geo}$
transport mean free path: $l_{tra}=(n_0\sigma pr)^{-1}$
reduced scattering coefficient: $\mu s'=1/l_{tra}$
attenuation length: $l_{att}=l_{tra}/\sqrt{(3(1-a)l_{tra}/(al_{sca}))}=\sqrt{(l_{tra}l_{in}/3)}$
absorption coefficient: $\mu_a=\mu_s(1-a)/a$
attenuation coefficient: $\kappa=\sqrt{(3\mu_a\mu_s')}=\sqrt{(3(1-a)/(al_{sca}l_{tra}))}=\sqrt{(3\mu_s'(l_{ext}^{-1}lsca^{-1}))}$ FIG. 6 shows the extinction efficiency $Q_{ext}$ and the efficiency of radiation pressure $Q_{pr}$ of water droplets (refractive index 1.33) in air (refractive index 1) as a function of size. This can be calculated by Mie theory, which provides an exact description of electromagnetic scattering from spherical objects.

The extinction efficiency initially rises rapidly with the size parameter $x$, has several maxima and minima and tends asymptotically to a constant with a decaying oscillation. The graphs in FIG. 6 represent the case of weak absorption (imaginary part of refractive index k=0 and albedo a=1), where $Q_{ext}=Q_{sca}$, but rigorous calculation of the scattering properties at wavelengths at which water does absorb strongly is standard within Mie theory.

Both the particle and medium refractive index are in fact complex numbers, n–ik, but in case of visible or NIR light with scattering from water droplets in air, the imaginary parts of both are very small compared to the real parts.

A dye can be added to increase the absorption or to introduce fluorescence. This would give extra parameters to measure and possibly increase sensitivity.

In the case of fully diffused light, the most opaque aerosol is found when the droplet size for a water/air mixture (mist) is between 5<x<15 were $Q_{pr}=0.6$ is at its maximum value, as can be seen in FIG. 6. The size parameter is $x=2\pi r\, n_{med}/\lambda$.

This implies droplet diameters of 1.24<d<3.72 micron. In the case of low optical density, such as the case for the nebulizer where the opacity is typically less than 30%, single scattering only can be assumed:

$$I=I_0\exp(-z/l_{ext})\approx I_0(1-z/l_{ext})$$

The distance z is known, and all of the aerosol has to pass through the beam, so small concentration differences will certainly not matter as long as the local opacity is low enough to prevent multiple scattering. Optical absorption does not play a significant role, so the extinction and scattering cross sections are equal ($Q_{sca}=Q_{ext}$).

It is straightforward to derive that $l_{ext}=2d/(3f\, Q_{ext})$.

Thus the light intensity measured by a detector in light path configurations A or C:

$$I\approx I_0(1-3f\, Q_{sca}z/(2d))$$

where $I_0$ is the detected intensity without aerosol in the beam path. The scattering cross section does not vary significantly over the range of particle diameters and is close to $Q_{sca}=2.4$, certainly given the distribution of sizes.

Effectively, measuring the intensity of transmitted or backscattered light provides a value related to f/d, the ratio of volume fraction and particle size.

If the particle size distribution is narrow enough, however, it is possible to estimate any change in particle size independently from a change in aerosol volume fraction $f=z\, d^3 n_0/6$, where $n_0=N/V$ (the number density of particles) and N the number of particles.

This can be achieved by using quite different illumination wavelengths $\lambda_1$ and $\lambda_2$ so that $Q_{sca}(\lambda)$ has a quite different slope at the same particle size, for example so that $x(\lambda_1)=13$ and $x(\lambda_2)=18$. FIG. 6 shows that these values give opposite slope in the $Q_{ext}(=Q_{sca})$ function. For a particle size of d=4 µm, with the size parameter being $x=\pi d n_{med}/\lambda$ and $n_{med}=1$, this would imply wavelengths of approximately $\lambda_1=967$ nm and $\lambda_2=698$ nm.

The invention involves the measurement of obscuration (or reflection, depending on the beam path chosen) at two or more wavelengths. Although in principle a tunable light source can be provided, in practice a respective light source will be provided for each selected wavelength, together with a corresponding detector tuned for detection at the corresponding wavelength. The two (or more) wavelength measurements can be taken simultaneously or in sequence, and they are preferably taken close together along the aerosol flow path so that the same volume fraction and particle size are present.

The time between measurements should preferably be small enough so that no significant movement of the aerosol has taken place. Typically this would be in the millisecond range.

It is possible to measure particle size absolutely if the distribution is narrow enough. If not, still a trend in change of particle size can be observed (a shift of the distribution of particle sizes).

FIG. 6 shows that Qext is approximately equal to 2.4 in the case of a broad distribution of particle sizes as is the case for the known nebulizer product. It is also possible to make aerosol generators that produce a narrow distribution, see for example the article "Miniaturized multiple Fourier-horn ultrasonic droplet generators for biomedical applications" as referenced above.

In the case of very narrow distribution of particle sizes, FIG. 6 shows the modulation (variation in Q) on the amount of light scattering as a result of particle size variation (changes in x). The variation Q translates into a variation in measured transmitted intensity I. In case of backscattering, a similar variation will be seen, but with the opposite sign.

The use of two wavelengths means that two measurements along the size parameter axis are taken. By fitting the two measurements to the curve, the position along the x-axis can be derived, and thereby the particle size d. The approximate particle size is also known from the design, as well as the way the particle size is expected to evolve with time, and this information can further assist in matching the measurement results to the curve of FIG. 6. Additional wavelengths can also be used to provide improved mapping of the results to the theoretical plots.

Typical values for the nebulizer are:
desired particle size: d=4 µm;
wavelength chosen: $\lambda=880$ nm;
(the corresponding size parameter is x=14.3)
source-detector distance: z=14 mm The volume fraction is equal to the fluid flow rate divided by aerosol flow rate: f=Df/Da. A typical aerosol flow rate is Da=30 l/minute and a typical fluid flow rate is Df=1 ml/minute.

The typical expected volume fraction is $f\approx 10^{-5}$ and the typical expected obscuration is $I-I_0\approx 10^4 f\approx 0.1$.

In FIG. 7, the aerosol particle size distribution (0.9% NaCl) is as produced by a commercially available nebulizer (the Philips Porta Neb) and measured by a Malvern Mastersizer, which uses a HeNe laser with a wavelength of λ=633 nm. The measured total obscuration is 15.8% and a D(v,0.5)=4.02 micron is found. This is a standard way to characterize particle distributions. The D stands for diameter, the v stands for volume fraction and the 0.5 indicates that 50% of the particles (by volume) and smaller than D, 4.02 micron in this case.

The detailed particle volume results have been used to calculate the obscuration for each given particle size.

FIG. 7 shows the aerosol volume fraction ("relative volume") per particle diameter and obscuration per particle diameter at a wavelength of 633 nm. Experimentally, the total sum of the obscurations is 0.158 as shown by the "cumulative obscuration" plot. Each particle results in some obscuration, which can be calculated exactly by Mie theory. The total obscuration is the sum of the obscuration of the individual particles in the aerosol.

In FIG. 8, the measured aerosol particle size distribution (0.9% NaCl) is used to calculate the total obscuration as a function of wavelength and particle size. The four plots are for different wavelength, as identified in units of μm. It appears that the total obscuration per wavelength varies only slightly: 15.8%, 15.8% 14.9% and 11.4% for wavelengths of 405 nm, 633 nm, 880 nm and 1650 nm respectively. The reason is that the particle distribution for the Porta Neb is too wide to show any significant resonance as a whole. From the figure it is however clear that such resonances do exist, i.e. for specific particle sizes, different wavelengths of light give very different obscuration measurement, so that a particular wavelength gives a peak obscuration level for a given particle size.

The above analysis shows that the obscuration will also not be very sensitive to changes in particle size, at least not through the variation in size parameter, since the size parameter depends equally on wavelength and particle size.

In conclusion, for a wide particle distribution, the obscuration seems mainly determined by the volume fraction of the aerosol. However, for a narrow particle size distribution, the use of multiple wavelengths enables the determination of the particle size from a combined set of measurements in transmission at different wavelengths.

Thus, if there is a wide distribution of particle sizes, the volume fraction can be derived, but if there is a narrow distribution, the actual particle size can be obtained.

Several detectors can be provided in a ring inside the mouthpiece, around the flow of aerosol. This enables measurement of the distribution of scattering angles of light in the mouthpiece. The particle size can then be measured independently. Measurements on scattered light (such as in configuration B) are more sensitive to wavelength and particle size. In particular, looking at light scattered at larger angles, for example near a right angle, the contribution from large particles in the distribution will diminish and thus enhance the visibility of small particles. This selection therefore narrows the effective width of the distribution. In FIG. 8, it is clear that the small particle end of the distribution shifts rapidly with wavelength or particle size and hence it can be used to determine the particle size more accurately. Simultaneous use of configurations A and B will help calibration and interpretation.

Nebulizers which can be controlled by the approach of the invention can be used for the treatment of Cystic Fibrosis, Asthma and COPD.

The invention enables optical sensing of particle size and density in a nebulizer mouthpiece. The optical arrangement can also be used to derive the aerosol flow rate, if the velocity is also obtained. As mentioned above, a flow meter can be used for this purpose.

However, both velocity and volume flow of aerosol can be measured optically. To do so, the aerosol density can be measured at two positions along the direction of flow in the mouthpiece, and the propagation of disturbances (fluctuations) in the aerosols are monitored and identified by cross-correlation of the signals with a variable time delay. Hence, the average wave speed for a travelling cloud of drops can be calculated. This is based on identifying the motion of a characteristic signal from one detector to the next. This relies on the aerosol cloud varying over time, so that the detector signal measured is a time varying signal. The PWM control of the nebuliser already provides a signal which fluctuates over time, so that cross correlation can be used to identify when the same light detector function (with respect to time) has reached a subsequent point in the aerosol flow direction.

Feedback can be given to the driver electronics to keep any of the mentioned parameters within the required bounds for proper medical dosage.

As outlined above, the measured light can be based on light scattering, absorption or fluorescence. For absorption, use of a dye, which is harmless to the patient, can give improved contrast in the transmission. This is especially advantageous if the liquid is at low concentration, or naturally quite transparent. For fluorescence, a fluorescent material, which is again harmless to the patient, is used and the light measurement is at a different wavelength than that of the source. This is especially advantageous if the liquid has at a low concentration and the signals may be weak or hard to distinguish from reflections or ambient light. The fluorescent light typically has a longer wavelength compared to the excitation light, and because it is radiated in all directions, it will be less dependent on the source-detector positioning. The detector then has an optical filter which passes only a band including the fluorescent light wavelength.

In all cases, the medicine or carrier thereof (usually water) may already have the required absorbing, scattering or fluorescent properties, if not extra dye may be added to the formulation.

In many of the above cases, knowledge of the light scattering properties of the droplets is required or at least beneficial. This is provided by Mie theory. Since the droplets are small, capillary forces will demand the droplets to be spherical. This is exactly the regime where this theory applies very accurately.

Extra information may be obtained by comparing polarized and depolarized scattering contributions; in particular, the amount of multiple scattering can be estimated by the degree of depolarization of the light. The ratio of scattered light polarized parallel to and perpendicularly to the linearly polarized light of the light source can be a measure of the aerosol density, in particular if the obscuration is low. At low obscuration, single scattering (which is polarization preserving) is more likely, and at high density and obscuration, multiple scattering causes scrambling of the polarization.

In the examples above, light from one or more LEDs is guided from the nebulizer body through the aerosol and back onto a photo detector. However, alternative embodiments may comprise optical fibers, mirrors, integrated mirrors working on Total Internal Reflection, lenses, lasers, etc.

Look up tables can be used, for example the average speed of the drops and liquid flux can be calculated from look-up tables, containing both the droplet density, and said average wave speed as input parameters.

The invention uses at least two different wavelength signals for detection. Increased accuracy may be obtained by using more than two different wavelengths.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. An aerosol measurement system, comprising:
   a flow device for generating an aerosol flow;
   a light source arrangement and a light detector for detecting light which has interacted with the aerosol flow;
   a controller for controlling the light source arrangement and for interpreting the detected light signals;
   wherein the controller is adapted to:
      control the light source arrangement to provide a first signal at a first wavelength and to record a first detected light signal;
      control the light source arrangement to provide a second signal at a second wavelength and to record a second detected light signal;
      process the first and second detected signals to derive a measure of the aerosol particle size by:
         processing the first and second detected signals to determine measurements of the obscuration at each of the first and second wavelengths;
         comparing the measurements of the obscuration at each of the first and second wavelengths to a function relating the modulation on the amount of light scattering by an aerosol flow to particle size variation; and
         deriving a measure of the aerosol particle size from the result of the comparison.

2. A system as claimed in claim 1, wherein the light detector is for detecting light which has passed through the aerosol flow.

3. A system as claimed in claim 2, further comprising a dye added to an aerosol liquid.

4. A system as claimed in claim 1, wherein the light detector is for detecting light which has been reflected or scattered by the aerosol flow.

5. A system as claimed in claim 4, further comprising a fluorescent additive added to an aerosol liquid.

6. A system as claimed in claim 1, wherein the controller is further adapted to derive the aerosol density from the detected light signals.

7. A system as claimed in claim 6, wherein the light source arrangement comprises light sources at different positions along the aerosol flow, and a detector is provided for each light source, wherein the controller is adapted to derive the aerosol velocity from the detected light signals at the different positions along the aerosol flow.

8. A system as claimed in claim 7, wherein the controller is adapted to determine a time delay of the aerosol flow between different positions along the aerosol flow by applying a cross correlation to the signals received at the different positions with a variable time delay.

9. A system as claimed in claim 1, wherein the light detector is adapted to separate polarized and depolarized light contributions to determine an amount of scattering.

10. A system as claimed in claim 1, further comprising a flow device controller for controlling the flow device, wherein the system comprises a feedback loop such that the flow device controller takes account of monitored parameters of the aerosol flow.

11. A method of measuring an aerosol, comprising:
    generating an aerosol flow;
    controlling a light source arrangement to provide a first signal at a first wavelength and recording a first detected light signal;
    controlling the light source arrangement to provide a second signal at a second wavelength and recording a second detected light signal;
    processing the first and second detected signals to derive a measure of the aerosol particle size:
    processing the first and second detected signals to determine measurements of the obscuration and each of the first and second wavelengths;
    comparing the measurements of the obscuration at each of the first and second wavelengths to function relating the modulation and the amount of light scattering to particle size variation; and
    deriving a measure of the aerosol particle size from the result of the comparison.

12. A method as claimed in claim 11, comprising detecting light which has passed through the aerosol flow, or detecting light which has been reflected or scattered by the aerosol flow.

13. A method as claimed in claim 11 comprising deriving the aerosol density from the detected light signals.

14. A method as claimed in claim 13, comprising deriving the aerosol velocity from the light signals at different positions along the aerosol flow, by applying a cross correlation to the signals received at the different positions along the aerosol flow with a variable time delay, thereby to determine a time delay of the aerosol flow between the different positions.

15. A method as claimed in claim 11, further comprising controlling the flow device using a feedback loop which takes account of monitored parameters of the aerosol flow.

* * * * *